(12) United States Patent  (10) Patent No.: US 7,909,861 B2
Balachandran et al.  (45) Date of Patent: Mar. 22, 2011

(54) CRITICAL CARE THERMAL THERAPY METHOD AND SYSTEM

(75) Inventors: Niran Balachandran, Lewisville, TX (US); Tony Quisenberry, Highland Village, TX (US); Darko Hadzidedic, Plano, TX (US); Overton L. Parish, Frisco, TX (US)

(73) Assignee: ThermoTek, Inc., Flower Mound, TX (US)

( * ) Notice: Subject to any disclaimer, the term of this patent is extended or adjusted under 35 U.S.C. 154(b) by 998 days.

(21) Appl. No.: 11/580,504

(22) Filed: Oct. 13, 2006

(65) Prior Publication Data

US 2007/0112401 A1 May 17, 2007

Related U.S. Application Data

(60) Provisional application No. 60/726,786, filed on Oct. 14, 2005.

(51) Int. Cl.
*A61F 7/00* (2006.01)
*A61B 5/01* (2006.01)

(52) U.S. Cl. ............................ 607/104; 607/96; 600/549
(58) Field of Classification Search .................... 607/104
See application file for complete search history.

(56) References Cited

U.S. PATENT DOCUMENTS

| 773,828 | A | 11/1904 | Titus et al. |
|---|---|---|---|
| 2,110,022 | A | 3/1938 | Kliesrath |
| 2,504,308 | A | 4/1950 | Donkle, Jr. |
| 3,014,117 | A | 12/1961 | Madding |
| 3,345,641 | A | 10/1967 | Jennings |
| 3,367,319 | A | 2/1968 | Carter, Jr. |
| 3,608,091 | A | 9/1971 | Olson et al. |
| 3,660,849 | A | 5/1972 | Jonnes et al. |
| 3,736,764 | A | 6/1973 | Chambers et al. |
| 3,738,702 | A | 6/1973 | Jacobs |
| 3,744,053 | A | 7/1973 | Parker et al. |
| 3,744,555 | A * | 7/1973 | Fletcher et al. .................. 165/46 |
| 3,862,629 | A | 1/1975 | Rotta |
| 3,894,213 | A | 7/1975 | Agarwala |
| 4,006,604 | A | 2/1977 | Seff |
| 4,013,069 | A | 3/1977 | Hasty |
| 4,459,468 | A | 7/1984 | Bailey |
| 4,459,822 | A | 7/1984 | Pasternack |
| 4,503,484 | A | 3/1985 | Moxon |
| 4,547,906 | A | 10/1985 | Nishida et al. |

(Continued)

FOREIGN PATENT DOCUMENTS

CH 670 541 6/1989

(Continued)

OTHER PUBLICATIONS

U.S. Appl. No. 11/801,662.

(Continued)

*Primary Examiner* — Roy D Gibson
*Assistant Examiner* — Kaitlyn E Helling
(74) *Attorney, Agent, or Firm* — Winstead PC

(57) ABSTRACT

A critical care thermal therapy system incorporating a remote temperature sensor in association with a thermal module adapted for delivering a fluid to a patient in response to the sensed temperature thereof.

35 Claims, 7 Drawing Sheets

U.S. PATENT DOCUMENTS

| | | |
|---|---|---|
| 4,660,388 A | 4/1987 | Greene, Jr. |
| 4,741,338 A * | 5/1988 | Miyamae ................. 607/112 |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,962,761 A | 10/1990 | Golden |
| 4,979,375 A | 12/1990 | Nathans et al. |
| 4,996,970 A | 3/1991 | Legare |
| 5,044,364 A | 9/1991 | Crowther |
| 5,051,562 A * | 9/1991 | Bailey et al. ................. 219/506 |
| 5,067,040 A | 11/1991 | Fallik |
| 5,080,089 A | 1/1992 | Mason et al. |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| 5,402,542 A | 4/1995 | Viard |
| 5,405,370 A | 4/1995 | Irani |
| 5,405,371 A | 4/1995 | Augustine et al. |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,507,792 A | 4/1996 | Mason |
| 5,509,894 A | 4/1996 | Mason et al. |
| 5,528,485 A | 6/1996 | Devilbiss et al. |
| 5,561,981 A | 10/1996 | Quisenberry et al. |
| 5,566,062 A | 10/1996 | Quisenberry et al. |
| 5,578,022 A | 11/1996 | Scherson et al. |
| 5,588,954 A | 12/1996 | Ribando et al. |
| 5,591,200 A | 1/1997 | Cone et al. |
| 5,648,716 A | 7/1997 | Devilbiss et al. |
| D383,547 S | 9/1997 | Mason et al. |
| D383,848 S | 9/1997 | Mason et al. |
| 5,662,695 A | 9/1997 | Mason et al. |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,155 A | 1/1998 | DeVilbiss et al. |
| 5,731,954 A | 3/1998 | Cheon |
| 5,755,755 A | 5/1998 | Panyard |
| 5,772,618 A | 6/1998 | Mason et al. |
| 5,782,780 A | 7/1998 | Mason et al. |
| 5,807,294 A | 9/1998 | Cawley et al. |
| 5,827,208 A | 10/1998 | Mason |
| 5,831,824 A | 11/1998 | McDunn et al. |
| 5,871,526 A * | 2/1999 | Gibbs et al. ................. 607/104 |
| 5,890,371 A | 4/1999 | Rajasubramanian et al. |
| 5,901,037 A | 5/1999 | Hamilton et al. |
| 5,923,533 A | 7/1999 | Olson |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D430,288 S | 8/2000 | Mason et al. |
| D430,289 S | 8/2000 | Mason et al. |
| 6,125,036 A | 9/2000 | Kang et al. |
| 6,129,688 A | 10/2000 | Arkans |
| 6,135,116 A | 10/2000 | Vogel et al. |
| 6,176,869 B1 | 1/2001 | Mason et al. |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,319,114 B1 | 11/2001 | Nair et al. |
| 6,358,219 B1 | 3/2002 | Arkans |
| 6,462,949 B1 | 10/2002 | Parish, IV et al. |
| 6,508,831 B1 * | 1/2003 | Kushnir ................. 607/104 |
| 6,551,264 B1 | 4/2003 | Cawley et al. |
| 6,596,016 B1 | 7/2003 | Vreman |
| 6,660,027 B2 * | 12/2003 | Gruszecki et al. ............. 607/104 |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,775,137 B2 | 8/2004 | Chu et al. |
| 6,789,024 B1 | 9/2004 | Kochan, Jr. et al. |
| 6,802,823 B2 | 10/2004 | Mason |
| 6,834,712 B2 | 12/2004 | Parish et al. |
| 6,848,498 B2 | 2/2005 | Seki et al. |
| 6,855,158 B2 | 2/2005 | Stolpmann |
| 6,893,414 B2 | 5/2005 | Goble et al. |
| 6,935,409 B1 | 8/2005 | Parish, IV et al. |
| 6,936,019 B2 | 8/2005 | Mason |
| 7,066,949 B2 | 6/2006 | Gammons et al. |
| 7,081,128 B2 | 7/2006 | Hart et al. |
| 7,306,568 B2 | 12/2007 | Diana |
| 7,429,252 B2 | 9/2008 | Sarangapani |
| 7,484,552 B2 | 2/2009 | Pfahnl |
| 2001/0039439 A1 | 11/2001 | Elkins et al. |
| 2002/0116041 A1 * | 8/2002 | Daoud ................. 607/105 |
| 2003/0089486 A1 | 5/2003 | Parish et al. |
| 2003/0089487 A1 | 5/2003 | Parish, IV et al. |
| 2003/0127215 A1 | 7/2003 | Parish, IV et al. |
| 2003/0135252 A1 * | 7/2003 | MacHold et al. ............. 607/106 |
| 2003/0163183 A1 * | 8/2003 | Carson ................. 607/108 |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0099407 A1 | 5/2004 | Parish, IV et al. |
| 2004/0193218 A1 | 9/2004 | Butler |
| 2004/0221604 A1 | 11/2004 | Ota et al. |
| 2004/0260231 A1 | 12/2004 | Goble et al. |
| 2005/0004636 A1 * | 1/2005 | Noda et al. ................. 607/105 |
| 2005/0006061 A1 | 1/2005 | Quisenberry et al. |
| 2005/0039887 A1 | 2/2005 | Parish, IV et al. |
| 2005/0070835 A1 | 3/2005 | Joshi |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0256556 A1 | 11/2005 | Schirrmacher et al. |

| | | |
|---|---|---|
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0137181 A1 | 6/2006 | Parish, IV et al. |
| 2006/0282028 A1 | 12/2006 | Howard et al. |
| 2007/0112401 A1 | 5/2007 | Balachandran et al. |
| 2007/0282249 A1 | 12/2007 | Quisenberry |
| 2008/0058911 A1 | 3/2008 | Parish et al. |
| 2008/0071330 A1 | 3/2008 | Quisenberry |
| 2009/0069731 A1 | 3/2009 | Parish et al. |
| 2009/0109622 A1 | 4/2009 | Parish et al. |
| 2009/0149821 A1 | 6/2009 | Scherson et al. |

FOREIGN PATENT DOCUMENTS

| | | |
|---|---|---|
| DE | 35 22 127 | 1/1987 |
| EP | 0 489 326 | 6/1992 |
| SU | 689674 | 10/1979 |
| WO | WO-93/09727 | 5/1993 |
| WO | WO-00/40186 | 7/2000 |

OTHER PUBLICATIONS

Artikis, T., PCT International Preliminary Report on Patentability as mailed Jul. 29, 2005, (10 pgs.).

Tom Lee, T.Y. et al; "Compact Liquid Cooling System for Small, Moveable Electronic Equipment", IEEE Transactions on Components, Hybrids, and Manufacturing Technology, Oct. 15, 1992, No. 5, pp. 786-793.

U.S. Appl. No. 12/708,422, Balachandran et al.

U.S. Appl. No. 12/730,060, Parish et al.

Copenheaver, Blaine R., International Search Report for PCT/US2007/022148 as mailed Apr. 2, 2008, 2 pages.

U.S. Appl. No. 12/176,084, Overton L. Parish.

Young, Lee W., "International Search Report" for PCT/US07/08807 as mailed Mar. 3, 2008, (2 pages).

U.S. Appl. No. 12/871,188, Parish et al.

Cyro/Temp Therapy Systems; Product News Catalogue; Jobst Institute, Inc., 6 pages (Copyright 1982).

* cited by examiner

CRITICAL CARE THERMAL THERAPY METHOD AND SYSTEM

CROSS REFERENCE OF RELATED APPLICATIONS

The present application claims priority to and incorporates by reference the entirety of U.S. Provisional Patent Application Ser. No. 60/726,786 filed Oct. 14, 2005 and cross references and incorporates by reference U.S. Published Applications No. 2006/0034053 filed Aug. 12, 2005 and U.S. Published Applications No. 2005/0143797 filed Jul. 19, 2004.

BACKGROUND OF THE INVENTION

1. Field of the Invention

The present invention relates to temperature control systems and methods and more particularly, but not by way of limitation, to critical care thermal therapy systems utilizing a temperature control module operated in conjunction with a remotely disposed monitoring system enhancing performance and reliability of the thermal control over a patient's body in a manner particularly suited for neonatal care and other critical care.

2. History of the Prior Art

Medical care providers have long recognized the need to provide warmth and/or cooling directly to patients as part of routine treatment and therapy. For example, faster and more efficient recoveries have been reported using cold therapy for orthopedic patients. Moreover, the benefits of warming patients undergoing surgery has been conclusively proven.

Several methods, devices, and systems have been developed that deliver temperature controlled fluids through pads or thermal blankets to achieve the above purpose. Typically these devices and systems have heating and/or cooling elements, a source for the temperature controlled fluid, a pump for forcing the temperature controlled fluid through the pad, blanket, or other patient cover and a thermal interface between the patient and the temperature controlled fluid. U.S. Pat. No. 4,884,304 to Elkins is directed to a mattress-cover device which contains liquid flow channels which provide the selective heating or cooling by conduction.

Cooling blankets have also been proposed such as the blanket disclosed in U.S. Pat. No. 4,660,388 to Greene. Greene discloses a cooling cover having an inflatable pad with plenum chambers at opposite ends thereof. Cool air is generated in a separate unit and directed to the pad and out a number of apertures on the underside of the pad and against the body of the person using the cover.

A disposable heating or cooling blanket is disclosed in U.S. Pat. No. 5,125,238 to Ragan, et al. which has three layers of flexible sheeting. Two of the layers form an air chamber and the third includes a comfortable layer for contact with the patient. Conditioned air is directed toward the covered person through a multiplicity of orifices in the bottom layers of the blanket. Another system is set forth and shown in U.S. Pat. No. 5,989,285, assigned to the assignee of the present invention.

More recently the advantages of thermal control have been realized for critical care patients such as neonatal babies and stroke victims. Accurate critical care with thermal therapy systems require not only a temperature controlled fluid, but also the monitoring of the body temperature of the patient. It is critical that a reliable thermal response is used to achieve the desired core body temperature. Several problems are inherent, however, in prior art systems which lack fast and accurate temperature control in response to monitored temperature values. Time delays can result in thermal overshoot by the system, reducing patient effectiveness.

The key issue in accurate temperature control is indeed providing a system which incorporates a monitoring system having real-time temperature reading and a system response in proportion to the thermal measurements taken for the patient being treated. In other words, a sensed temperature of the patient's body evokes a thermal response which is directly associated therewith and without a time delay therefrom. Time delays between the detection of a denied thermal deviation and the delivery of the necessary heat or cold can, as referenced above, be deleterious. A system which provides the delivery of the necessary heat or cold within a short response period is necessary for true critical care through thermal therapy. It is therefore important that modem thermal therapy systems reduce the time differential substantially in order to afford the delivery of the necessary heat or cold to the patient's body for the requisite therapeutic effect.

It should be further noted that thermal therapy in critical care situations may be required in mobile intensive care units. Strokes often occur away from hospitals and comprise the genesis of basic lifesaving scenarios of the type where thermal therapy may be a critical life, or quality of life, saving factor. If an effective critical care thermal therapy system is not provided in a mobile configuration operable with multiple forms of power (such as AC and/or DC current) the utilization of the system is limited. The availability of a critical care system should not be dependent upon a single form of power.

The present invention addresses these considerations and affords an improvement over the prior art by providing an efficient thermal therapy system with real-time feedback monitored thermal response to uniformly heat or cool fluid delivered to a patient when and where the patient is in need. The present invention further includes a system that is operable on both AC and/or DC current and in an optionally portable configuration to facilitate use within automobile, care flight and other mobile configurations.

SUMMARY OF THE INVENTION

The present invention relates generally to a critical care thermal therapy system and method providing a patient with both recirculating temperature controlled fluid and real time monitoring and response to improve performance parameters and enhance patient care.

In one aspect, the present invention provides a portable critical care thermal therapy system, operable on multiple forms of electrical power for providing direct thermal therapy in response to a monitored temperature of the patient for accurate thermal control and treatment.

In yet another embodiment, the present invention provides a thermal therapy system combining Thermo Electric Components (TEC) for the generation of heat and cold as necessary for thermal therapy. TEC devices are assembled to run on DC current which may be provided by a battery or a converter from AC current. In this manner, the TEC system will support thermal therapy in mobile situations.

In yet another aspect, the present invention relates to a neonatal critical care thermal therapy system affording low noise and low vibration operation.

In yet another aspect, the present invention includes a system incorporating temperature monitoring of the patient through at least one of rectal temperature measurements, esophageal temperature measurements, skin temperature measurements, and/or deep brain temperature measurements. The system may be provided in a rack mount configuration or in a portable configuration while providing a treatment fluid having the necessary temperature and thermal capacitance to heat or cool large or small areas of a patient. The area of the patient can be limited to that of a specific region comprising a thermal wrap of limited size or a complete blanket such as that set forth as shown in above referenced U.S. Pat. No. 5,989,285 assigned to the assignee of the present invention and incorporated herein, in its entirety, by reference. Other thermal treatment units may be incorporated therewith in accordance with the principles of the present invention.

In a further aspect, the present invention includes a critical care, thermal therapy system utilizing a thermal fluid flow to which a patient is thermally exposed. The system comprises a recirculating, temperature controlled fluid flow network adapted for patient care, a temperature control module connectable in fluid communication with the temperature controlled fluid flow network for regulating the thermal fluid temperature and flow to the patient, a thermal therapy device adapted for the flow of the thermal fluid therethrough and thermal exposure to the patient, the device being connectable to the temperature control module through the temperature controlled fluid flow network, and at least one temperature sensor in thermal communication with the patient and remotely disposed from the temperature control module. In one embodiment, the at least one remotely disposed temperature sensor monitors a select body temperature and sends thermal measurement signals to the temperature control module and in another embodiment, the temperature control module is adapted to increase or decrease the control fluid temperature and flow rate in response to the thermal measurement signals from the at least one remotely disposed temperature sensor.

In yet a further embodiment, the above described embodiment, the thermal measurement signals sent by the at least one remotely disposed temperature sensor comprises real-time measurements, and further comprises a user interface coupled to the temperature control module for setting a desired temperature and tolerance boundaries wherein the tolerance boundaries represent upper and lower thermal fluid temperature limits.

In a preferred embodiment, the user interface is electrically isolated from the temperature control module and the temperature control module is adapted for continually adjusting the thermal fluid temperature such that the monitored temperature approaches the desired temperature.

In a still further aspect, the present invention includes a method of thermal therapy critical care with utilizing a thermal fluid flow to which a patient is thermally exposed, the method comprising the steps of recirculating a control fluid through a closed-loop fluid flow network adapted for patient care, adjusting the temperature of the thermal fluid with a temperature control module connectable to the fluid flow network controlling the flow of the thermal fluid with the temperature control module, thermally exposing an environment to the thermal fluid via a thermal therapy device connectable to the fluid flow network, monitoring a patient temperature with at least one temperature sensor remotely disposed from the temperature control module, and sending real-time signals from the at least one remotely disposed temperature sensor to the temperature control module indicating the patient temperature. In one embodiment, the at least one remotely disposed temperature sensor is electrically isolated from a main power supply of the temperature control module.

BRIEF DESCRIPTION OF THE DRAWINGS

Other advantages and features of the invention will become more apparent with reference to the following detailed description of a presently preferred embodiment thereof in connection with the accompanying drawings, wherein like reference numerals have been applied to like elements, in which.

DETAILED DESCRIPTION

Figure 1:
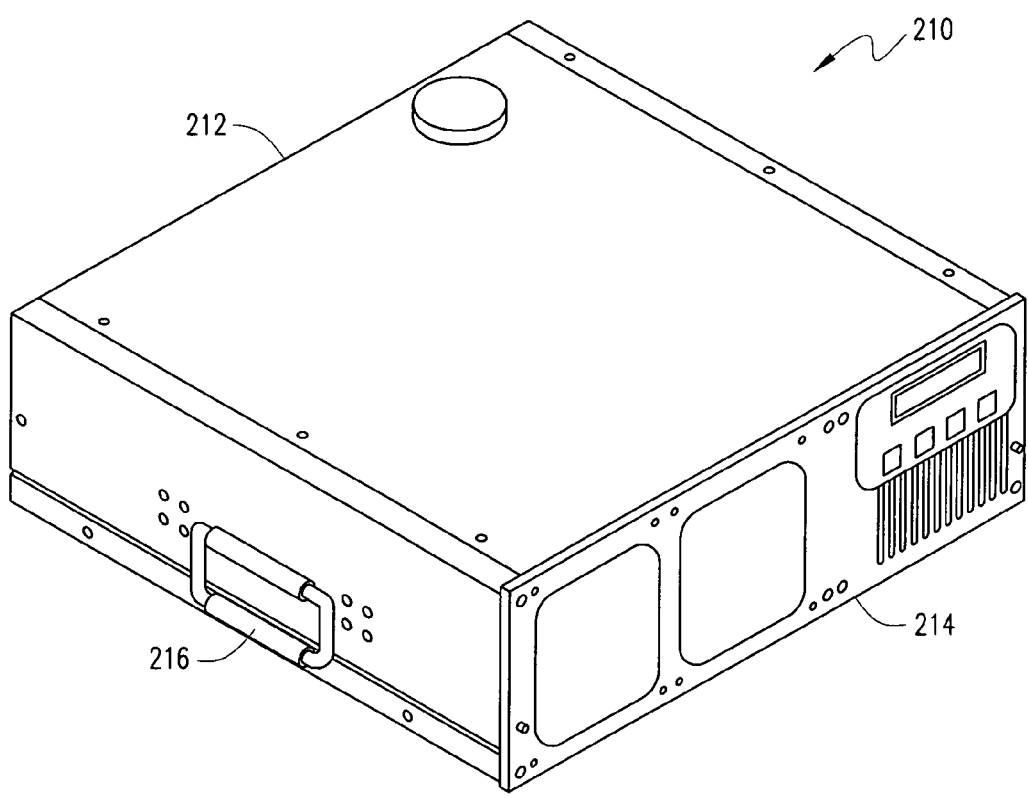
FIG. 1 is a perspective view of a critical care thermal therapy system controller for use with one or more remote temperature sensors and a fluid flow network, including a thermal therapy cover, pad or wrap utilized as a thermal treatment device as described herein.

The present invention relates to a critical care thermal therapy system having improved performance characteristics. Referring now specifically to the drawings, and in particular to FIG. 1, there is shown a thermal control unit 210 capable of providing a flow of liquid at the necessary flow rate to control the temperature of a thermal blanket or similar covering for the patient. For example, a temperature control blanket such as that set forth and shown in U.S. Pat. No. 5,989,285 could be incorporated for use herewith. It should be noted however that other patient coverings such as wraps, blankets and pad designs may be utilized in conjunction with the principles of the present invention.

Still referring to FIG. 1, the thermal control unit 210 of the present invention includes chassis 212 having control panel 214 disposed across a frontal portion thereof. The thermal control unit 210 is further constructed with a handle 216 disposed upon a side region therealong to facilitate handling. It should be noted that the thermal control unit 210 may be of the type set forth, shown, and described in U.S. patent application Ser. No. 11/202,885, the entirety of which is incorporated herein by reference. The 3U design of that particular invention is set forth and shown herein for reference purposes only and other size and operation configurations may be utilized. For purposes of reference, however, the teachings set forth shown and described in the above referenced U.S. patent application Ser. No. 11/202,885 are submitted to further enable one of ordinary skill in the art to construct the invention as hereinafter described. For example, the thermal capacity of the thermal control unit 210 may be selected in conjunction with temperature and flow conditions as shown in the specification sheet provided in the above-referenced patent application. The availability for select operation parameters for the thermal control unit 210 including, for example, up to six internal fan assemblies and an additional three internal fans with external fan trains and the like permit the designer and/or ultimate end-user the ability to specify the requisite operational parameters as well as AC or DC power source (or both) for the functional operation.

Still referring to the 3U system described above, multiple advantages are afforded for both customer and user in conjunction with the present invention. For example, the critical care thermal therapy system of the present invention may utilize, in certain embodiments, rack mounting configurations. One such configuration might include hospital applications. In other applications wherein portability is desirable, and DC power converter modules are available, the ability to utilize the system of the present invention and/or have the system upgraded for selective operation and selective emergency environments provide enumerable advantages over many prior art systems.

Still referring to FIG. 1, the chassis 212 shown herein may also be of a different dimension than the 3U dimension described above. The dimension may vary dependent upon the quantity of cooling engines selected and utilized therewith. The cooling engines shown and described herein utilize a peltier effect and incorporate TEC thermal modules. TEC modules allow for portable DC use. With DC use, a power converter may be provided, such as that shown in FIG. 4. The unit is operable with a patient covering such as the blanket set forth and described in the patent application, while monitoring the temperature of the patient with remote modules 300 the type shown in FIG. 5. As discussed below, the remote modules 300 of FIG. 5 are electrically isolated from the thermal control unit 210 to therein reduce the possibility of electric shock to the patient. This operational parameter is provided with both portable and rack mounted configurations.

Figure 2:
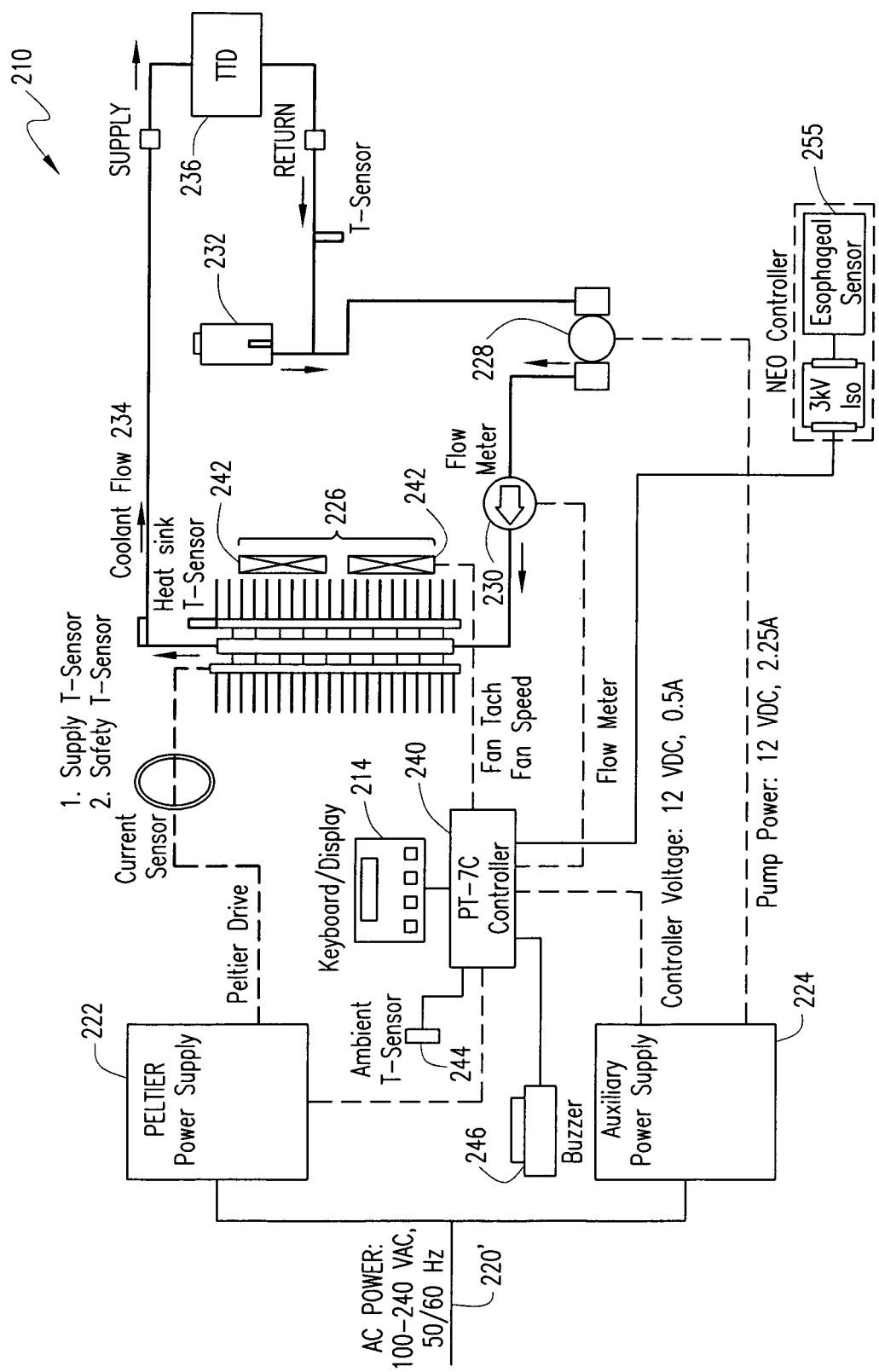
FIG. 2 is a functional block diagram of the thermal therapy system controller of FIG. 1 illustrating the functionality thereof in conjunction with remote sensors used therewith.

Referring now to FIG. 2 there is shown a functional block diagram of the thermal control unit 210. This particular unit is powered by AC power 220' allowing a peltier power supply (PPS) 222 and auxiliary power supply (APS) 224 to operate. The PPS 222 supplies current to a thermal engine 226. An operation mode of cooling is shown herein but the thermal control unit 210 may also utilize heat. In operation, the thermal engine 226 takes fluid from a coolant pump 228 via a flow meter 230. The coolant pump 228 pulls from reservoir 232, which collects fluid returning from a thermal therapy cover pad or blanket hereinafter referred to as a Thermal Therapy Device (TTD) 236. The output of engine 226 is coolant flow 234 that feeds the TTD 236.

Still referring to FIG. 2, the coolant pump 228 may be powered by APS 224 as indicated. It may also supply micro-controller 240 with requisite power. The micro-controller 240 regulates the flow through the flow meter 230 via the pump 228. With micro-controller 240 the speed of fans 242 is also regulated to control the flow of air thereacross and thus the heat transfer therefrom. The reading from the various sensors is then indicated on a control panel 214. Ambient sensors 244 are also utilized with a buzzer 246 to alert attendants in the event of operational issues.

Still referring to FIG. 2, a sensor 255 is shown as an esophageal sensor which may be utilized. As described above, other sensors are contemplated in accordance with to the principles of the present invention.

Figure 3:
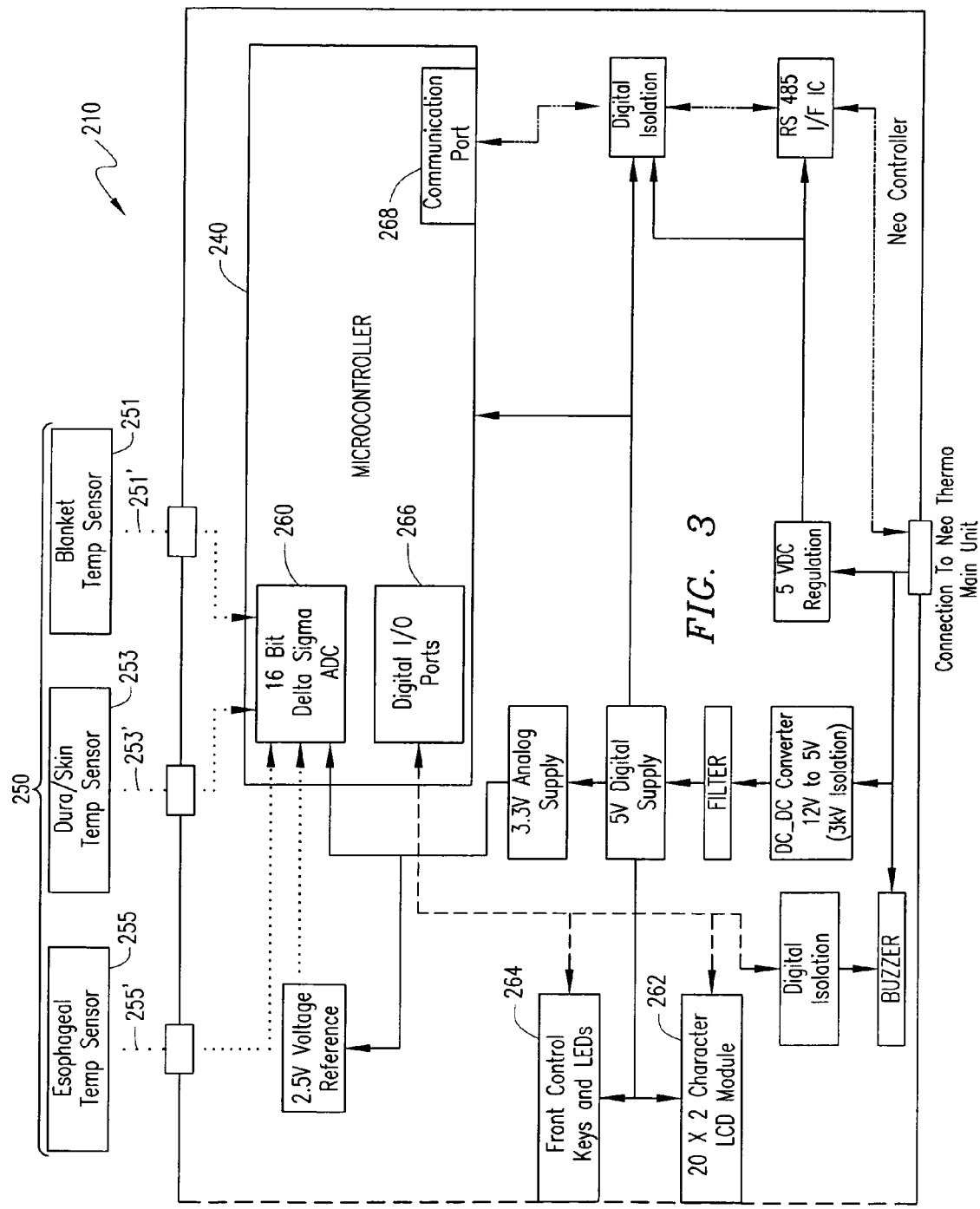
FIG. 3 is a block diagram of the operational aspects of the thermal therapy system controller of FIG. 1 illustrating the interactive functionality with a microcontroller incorporated therewith.

Referring now to FIG. 3, there is shown a thermal control unit block diagram. The thermal control unit 210 is electrically isolated from the array 250 of sensors used to monitor temperature of the patient. Array 250 comprises TTD blanket sensor 251, duraskin sensor 253 and esophageal sensor 255. These sensors as well as others could be provided for direct communication with the controller. The communication link may be through direct connection, infrared, and/or other remote communication systems. For purpose of example, connections are illustrated by dotted lines 251', 253' and 255'. The data from the sensors are then received by the micro-controller 240 which may include an analog/digital converter 260. The data is processed to determine patient temperature and fluid temperature. An illustrative algorithm for making these calculations is described below.

Core Temperature Adaptive Control

One of the primary functions of a control loop includes using the temperature data read from a sensor, for example an esophageal sensor, placed in proximity to the patient, to precisely control the cool down and warm up of the patient's core body temperature. The purpose of this exemplary algorithm is to reach the esophageal set point temperature (core body temperature) rapidly with minimum overshoot (<0.5 deg C.) and control the temperature at set point to with +/−0.2 deg C.

The control algorithm may also be able to auto-tune and adapt for variables such as patient weight, probe placement, sensor artifacts due to movement by the patient, temperature spikes due to IV's or meds, acid reflux and variation in metabolic conditions of the patient.

Control Method:

For exemplary purposes, a control method utilizing an esophageal temperature sensor will be described, but other thermal sensors monitoring other temperatures could also be utilized. The esophageal temperature sensing module may use a moving average computation to determine the esophageal temperature. It may also calculate the rate and acceleration factors for the temperature (first and second derivatives respectively).

This information may be used by the esophageal control loop to determine the optimal coolant, for example a blanket, temperature to be delivered to the patient as to achieve the desired core temperature.

In one exemplary embodiment, the esophageal adaptive control uses the esoph_error (defined as esophageal temp—esophageal set temp) to as the primary factor in determining the controller output computation. If the esoph_error is positive, the control output will apply cooling and if negative heating will be provided.

For both COOL and HEAT modes, there are four states:

STABLE State: If the esoph_error is within 0.25 deg C. of esophageal set point.

SLOW State: This state is applied when the esoph_error is >0.25 deg C. but<=1.00 deg C.

MEDIUM State: This is applied when the esoph_error is >1.00 deg C. but<=2.00 deg C.

FAST State: If the esoph_error is >2.00 deg C.

Within each state, the algorithm uses the temperature rate and second derivative information to adjust the coolant set temperature of the therapy unit. By using the esophageal temperature characteristics this algorithm changes the set temperature of the coolant (UP or DOWN) and lets the Supply Temperature Adaptive Control algorithm control the fluid temperature delivered to the patient.

The rate information may be used to determine the magnitude of coolant set temperature adjustment. This adjustment can be, for example, from +/−0.01 deg C. to 1.00 deg C. The second derivative gives useful information of change of temperature rate; this may be used to detect sudden temperature artifacts such as administration of meds or patient movement. If such events are detected, the control algorithm maintains the previous control parameters until the transient event has passed. Use of the second derivative allows the controller to not react to transients, thus minimizing temperature oscillations of core body temperature.

Supply Temperature Adaptive Control

This control loop maintains the coolant (supply) temperature of the therapy unit to within +/−0.1 deg C. of coolant set temperature.

The control loop calculates the control error by subtracting the measured temperature from the set temperature. If the error is positive the Proportional-Integral (PI) control will be in COOL mode and if negative it will operate in HEAT mode.

For both COOL and HEAT modes, these are three fuzzy stages for each mode.

Stage 1—MAX Drive: If the control error is greater than or equal to 2.00 deg C. then the Tec's are driven at maximum power to achieve setpoint condition. This mode is primarily to provide rapid response to changing set points or thermal conditions.

Stage 2—CONTROL Drive: If the control error is greater than 0.1 deg C. but less than 2.00 deg C., the TEC drive is proportional to the control error. This is a unique way to achieve quick settling time as the coolant temperature nears the set point, the magnitude of the control error will also decrease. Due to the linear relationship between the control error and TEC drive, the drive level will also reduce. This method dampens any temperature overshot, and minimizes temperature oscillations at set point.

Stage 3—STABLE Drive: If the control error is less than 0.1 deg C., the Tec's drive is turned OFF and the temperature is allowed to coast at or near set point.

Supply Temperature Adaptive Control (Optimization Loop)

If the PI control is in stage 2 or 3, this module may look at the average control error over a given time interval, and update the PI loop to drive the error to less then 0.05 deg C. The level of adjustment may be determined by the magnitude of the error and rate of change of the error (first derivative).

Information may be displayed on LCD 262 where keys and input controls 264 are connected to the micro-controller 240 through digital input/output ports 266. A communication port 268 provides control of heating/cooling engine 226 and flow meter 230.

Figure 4:
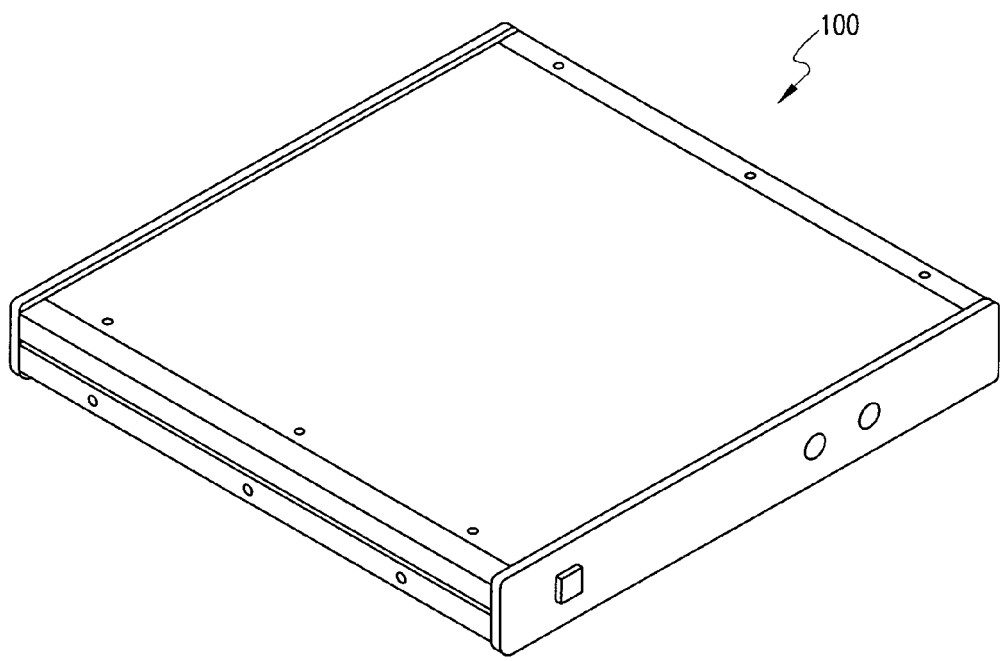
FIG. 4 is a perspective view of a DC power converter module for use in conjunction with the thermal therapy system controller of FIG. 1.
Figure 5:
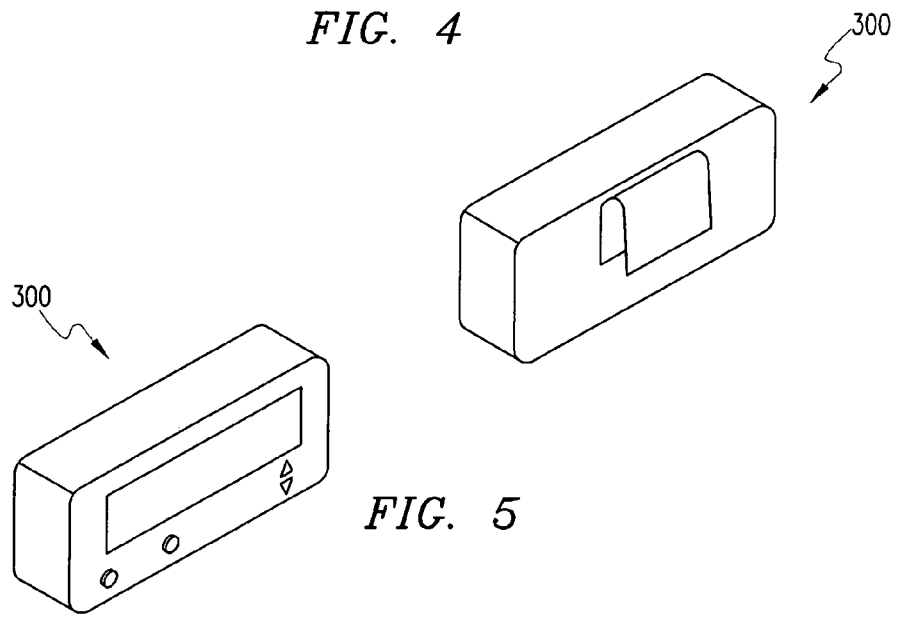
FIG. 5 is a perspective view of two remote sensing modules facing in opposite directions for illustrating the utilization therewith in conjunction with the thermal therapy system controller of FIG. 1.

Referring now to FIG. 4 there is shown a DC power converter module 100 as referenced above for use in conjunction with a portable aspect of the present invention. Likewise, FIG. 5 illustrates two remote sensing modules 300 of the type utilized to detect critical patient temperature and communicate with the control unit 210 of FIG. 1 to control the flow of fluid as described in FIGS. 2 and 3.

In operation, the individual operating the control unit 210 turns it on, chooses heat or cold and inputs the desired temperature via the input controls 264 on control panel 214. Control signals from control unit 210 are input to engine 226 and to pump 228 for control thereof. Temperature feedback from sensor array 250 is transmitted to micro-controller 240 as described above.

Temperature controlled liquid flows from the heating/cooling engine 226 to the TTD 236. TTD 236 and flow system which may be used with the present applications may be seen in U.S. patent application Ser. No. 10/894,369 incorporated herein by reference. It will be appreciated that the flow of temperature control liquid is therefore provided to a patient in need of thermal therapy care.

The following operational aspects are specifically referenced herein relative to the subject application. The present invention provides portability, accuracy, and temperature monitoring with increased real response time to provide improved patient care. Prior art systems attempting to provide thermal therapy to patients often manifested overshoot inefficiency problems. Overshoot is one of the more critical aspects from the standpoint of patient care under thermal therapy. With both stroke and neonatal patients, the need for real-time temperature control and the requisite thermal therapy within predefined tolerance boundaries is critical. For this reason, multiple aspects of temperature measurement of the patient is anticipated with the remote modules of the present invention affording doctors the ability to take temperatures such as rectal as well as esophageal and/or deep brain in addition to dermal. The remote sensing protects the patients and insulates the patient from any risks relative to power being supplied thereto, in this way, the patient is not exposed to the power supply. In one embodiment referred to above with a rack mount, the patient is able to experience the benefits of the system and thermal therapy in a low-noise, low-vibration environment. This may be very critical in neonatal units.

In summary, the AC/DC options of the present invention, as well as the size and weight of the thermal control unit 210, provide great benefits in association with the low noise and possibility for MICU ambulance/helicopter care.

With regard to neonatal applications it is important to note that premature infants typically cannot regulate their own body temperature and therefore the ability to accurately control thermal therapy systems with immediate response is a market advantage over the prior art. Feedback with multiple remote sensors is thus critical to the operation of the thermal engine 226 and the ability to provide larger thermal capacity by modifying the number and/or size of the thermal engine within the chassis 212 is of distinct importance. While particular embodiments of the present invention have been described, it will be appreciated by those skilled in the art that various modifications, alternatives, variations, etc., may be made without departing from the spirit and scope of the invention as defined in the appended claims.

Figure 6:
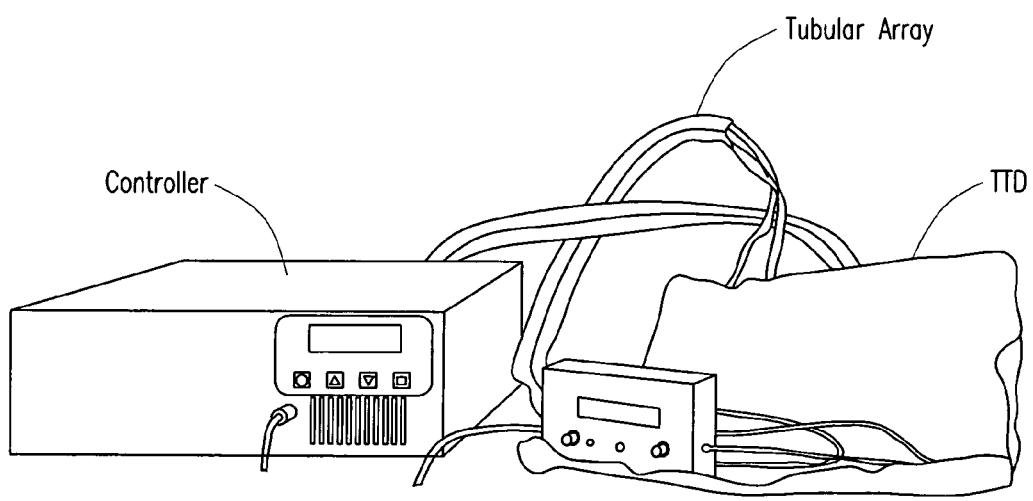
FIG. 6 is a perspective view of one embodiment of the system of the present invention.

Referring now to FIG. 6, there is shown a perspective view of the control unit 210 of FIG. 1 and the critical care system described above connected thereto. The control unit 210 is shown coupled to a tubular array providing the flow of fluid to a thermal blanket (TTD). In this particular test embodiment, a sensor is illustrated with direct connection to the controller. In actual operation, the sensor or sensors may be remote so that the patient does not have any direct electrical connectivity to the control unit 210 or a direct connection with appropriate safety isolation may be used. In this manner the possibility of shock should be substantially eliminated.

Figure 7:
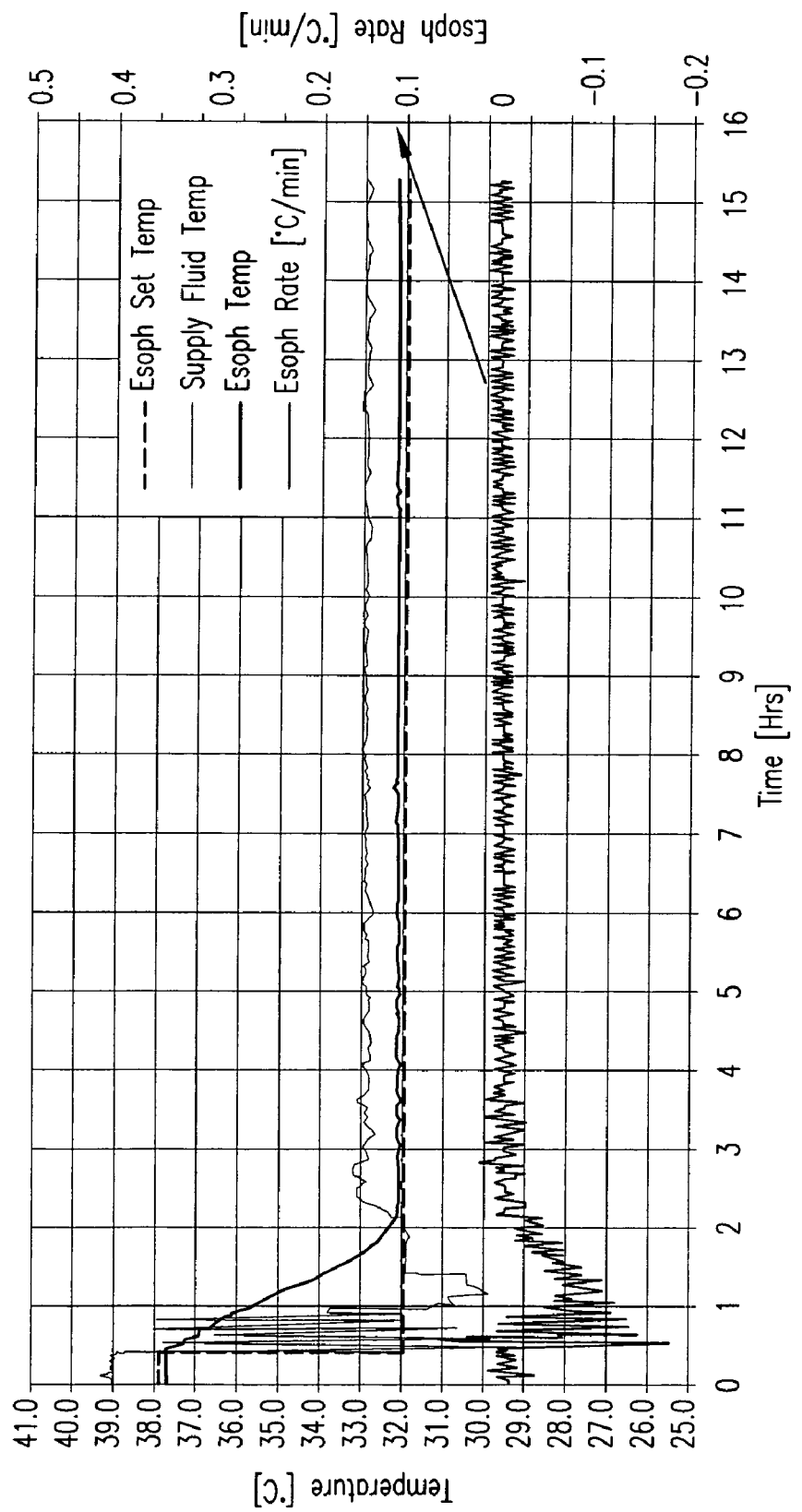
FIG. 7 is a chart presenting performance data.

FIG. 7 comprises neo-thermo performance data bench testing information relative to the principles of the present invention. The neo-thermo test set up utilized a stainless steel reservoir is used with a crib blanket. An immersion heating element was used as the thermal load and an esophageal temperature sensor was used to monitor the fluid temperature within the reservoir. The reservoir was filled with liquid detergent, which was found to conduct heat at a slower rate than water and perhaps provide a better test relative to data to be applied to human testing parameters. Temperature stability charts illustrating the relationship between the esophageal set temperature, the measured esophageal temperature, the supply fluid temperature and the esophageal rate are shown.

Still referring to FIG. 7, the chart provided illustrate the improved efficiency relative to thermal therapy treatment afforded by the present invention. The stability charts illustrate the fact that the present invention maintains the desired temperature in a uniform and stable fashion. The chart relative to the test set-up for the neo-thermo temperature system illustrate an esophageal temperature that is very stable and accurately maintained.

Figure 8:
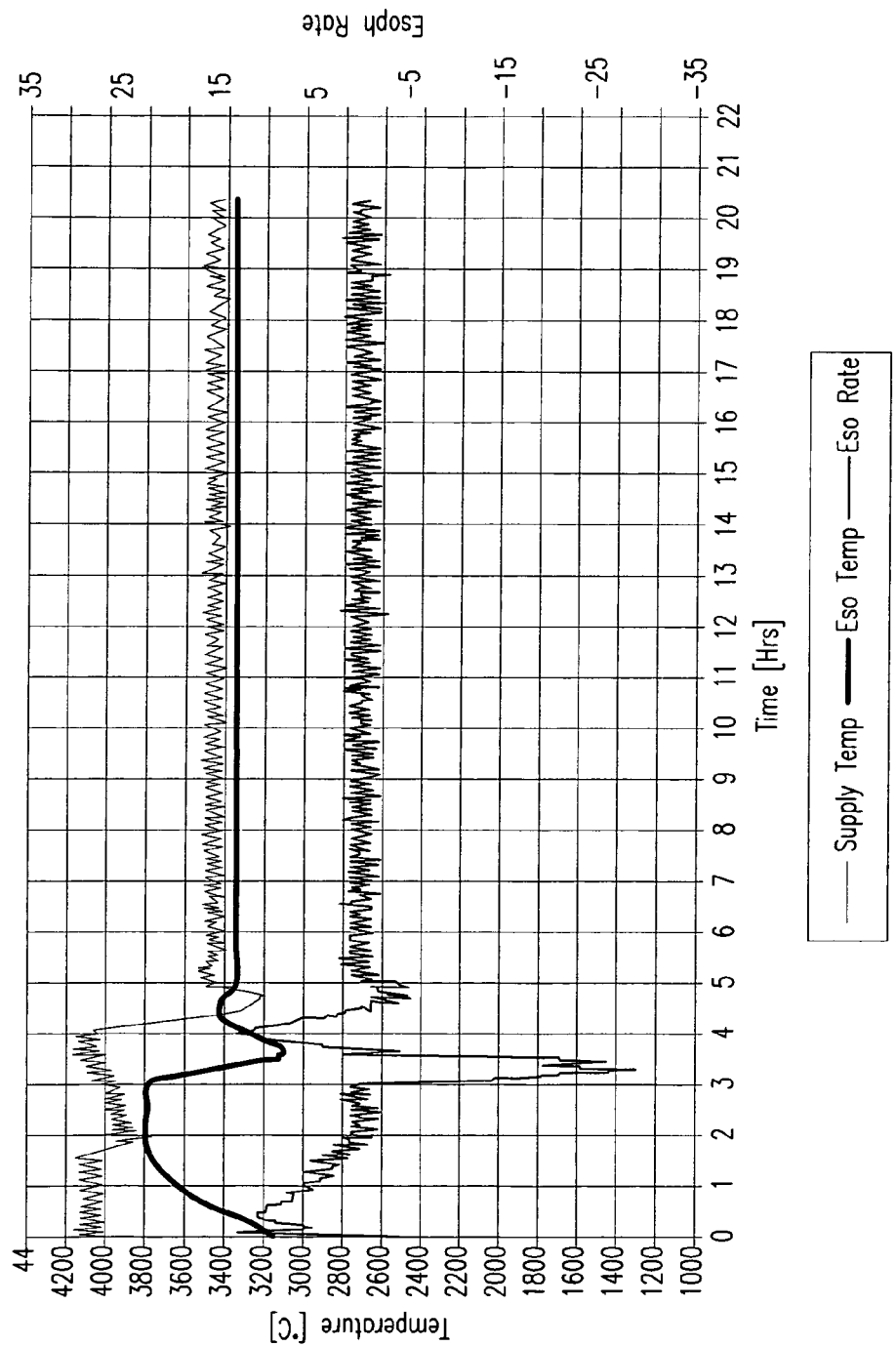
FIG. 8 is a chart of additional performance data related to the present invention.

FIG. 8 comprises a chart illustrating additional temperature stability readings relative to the supply temperature, the esophageal temperature as well as the esophageal rate. The Figure shows a temperature spike or transient event and the response thereto.

It is believed that the operation and construction of the present invention will be apparent from the foregoing description of a preferred embodiment. While the device shown is described as being preferred, it will be obvious to a person of ordinary skill in the art that various changes and modifications may be made therein without departing from the spirit and scope of the invention as defined in the following claims. Therefore, the spirit and the scope of the appended claims should not be limited to the description of the preferred embodiments contained herein.

What is claimed is:

1. A critical care, thermal therapy system utilizing a thermal fluid flow to which a patient is thermally exposed, the system comprising:
   a recirculating, temperature controlled fluid flow network adapted for patient care;
   a temperature control module connectable in fluid communication with the temperature controlled fluid flow network for regulating the thermal fluid temperature and flow to the patient;
   a thermal therapy device adapted for the flow of the thermal fluid therethrough and thermal exposure to the patient, the device being connectable to the temperature control module through the temperature controlled fluid flow network; and
   at least one temperature sensor in thermal communication with the patient and remotely disposed from the temperature control module;
   wherein the at least one remotely disposed temperature sensor monitors a select body temperature and sends thermal measurement signals to the temperature control module;
   wherein, the temperature control module calculates a rate factor and an acceleration factor of the select body temperature; and
   wherein, responsive to the rate factor and the acceleration factor of the select body temperature, the temperature control module is adapted to increase or decrease the thermal fluid temperature or flow rate in response to the thermal measurement signals from the at least one remotely disposed temperature sensor.

2. The system of claim 1 wherein the thermal measurement signals sent by the at least one remotely disposed temperature sensor comprise real-time measurements.

3. The system of claim 1 and further comprising:
   a user interface coupled to the temperature control module for setting a desired temperature and tolerance boundaries;
   wherein the tolerance boundaries represent upper and lower thermal fluid temperature limits.

4. The system of claim 3 wherein the user interface is electrically isolated from the temperature control module, by way of an infrared connection.

5. The system of claim 3 wherein the temperature control module continually adjusts the thermal fluid temperature wherein the monitored temperature approaches the desired temperature.

6. The system of claim 3 wherein the user interface comprises an alarm for alerting the user when an error occurs.

7. The system of claim 1 wherein the temperature control module is capable of receiving power from an AC power source.

8. The system of claim 1 wherein the temperature control module is capable of receiving power from a DC power source.

9. The system of claim 1 wherein the temperature controlled fluid flow network is portable.

10. The system of claim 1 wherein the temperature control module is rack mountable.

11. The system of claim 1 wherein the at least one remotely disposed temperature sensor is electrically isolated from the temperature control module, by way of an infrared connection.

12. The system of claim 1 wherein the at least one remotely disposed temperature sensor and the temperature control module are communicatively coupled via infrared signals.

13. The system of claim 1 wherein the temperature control module comprises a thermoelectric component for regulating the thermal fluid temperature.

14. The system of claim 13 wherein the thermoelectric component for regulating the temperature of the thermal fluid is secured therein for low-noise and low-vibrational operation facilitating use in a neonatal critical care environment.

15. The system of claim 1 wherein the at least one remotely disposed temperature sensor monitors one or more of a rectal temperature, an esophageal temperature, a dermal temperature, and a deep-brain temperature.

16. The system of claim 1 wherein the thermal therapy device comprises one or more of a thermal wrap, a thermal blanket, and a thermal pad.

17. The system of claim 1 and further comprising an alarm for indicating the occurrence of an error.

18. A method of thermal therapy critical care utilizing a thermal fluid flow to which a patient is thermally exposed, the method comprising:
   recirculating a thermal fluid through a closed-loop fluid flow network adapted for patient care;
   controlling the flow of the thermal fluid with a temperature control module connectable to the fluid flow network;
   thermally exposing an environment to the thermal fluid via a thermal therapy device connectable to the fluid flow network;
   monitoring a patient temperature with at least one temperature sensor remotely disposed from the temperature control module; and
   sending real-time signals from the at least one remotely disposed temperature sensor to the temperature control module indicating the patient temperature, wherein the temperature control module calculates a rate factor and an acceleration factor of the patient temperature; and
   adjusting a temperature of the thermal fluid responsive to the rate factor and the acceleration factor of the patient temperature via the temperature control module.

19. The method of claim 18 wherein the at least one remotely disposed temperature sensor is electrically isolated from a main power supply of the temperature control module, by way of an infrared connection.

20. The method of claim 18 and further comprising:
   inputting a desired temperature into a user interface coupled to the temperature control module.

21. The method of claim 20 and further comprising:
   inputting upper and lower tolerance boundaries into the user interface; and
   wherein the upper tolerance boundary represents a maximum allowed temperature for the thermal fluid and the lower tolerance boundary represents a minimum allowed temperature for the thermal fluid.

22. The method of claim 20 and further comprising:
decreasing the flow rate of the thermal fluid when the patient temperature substantially equals the desired temperature.

23. The method of claim 18 wherein a main power supply of the temperature control module is adapted to receive an AC input.

24. The method of claim 18 wherein a main power supply of the temperature control module is adapted to receive a DC input.

25. The method of claim 18 wherein the at least one remotely disposed temperature sensor and the temperature control module are communicatively coupled via infrared signals.

26. The method of claim 18 wherein the temperature control module utilizes a thermoelectric component to heat and cool the thermal fluid.

27. The method of claim 18 wherein the at least one remotely disposed temperature sensor is one of a rectal thermometer, an esophageal thermometer, a dermal thermometer, and a deep-brain temperature monitor.

28. The method of claim 18 wherein the thermal therapy device is one of a thermal wrap, a thermal blanket, and a thermal pad.

29. The method of claim 18 and further comprising:
sounding an alarm if any error occurs.

30. A critical care, thermal therapy system utilizing a thermal fluid flow to which a patient is thermally exposed, the system comprising:
a recirculating, temperature controlled fluid flow network adapted for patient care;
a temperature control module connectable in fluid communication with the temperature controlled fluid flow network for regulating the thermal fluid temperature and flow to the patient;
a thermal therapy device adapted for the flow of the thermal fluid therethrough and thermal exposure of the patient, the device being connectable to the temperature control module through the temperature controlled fluid flow network; and
a temperature sensor in thermal communication with the patient and remotely disposed from the temperature control module;
wherein the temperature sensor monitors a select body temperature and sends thermal measurement signals to the temperature control module; and
wherein the temperature control module utilizes a rate factor and an acceleration factor of the monitored temperature as well as a moving average of the monitored temperature to control the thermal fluid temperature or flow rate.

31. The thermal therapy system of claim 30 wherein the temperature control module waits for transient events to pass before making adjustments to the temperature of the thermal fluid.

32. The thermal therapy system of claim 31 wherein the temperature control module utilizes the acceleration factor of the monitored temperatures to calculate the rate of temperature change to detect transient events.

33. The thermal therapy system of claim 32 wherein the transient events comprise spikes in the monitored temperature due to one or more of movement of the patient, insertion of an I.V. into the patient, acid reflux in the patient, and a variation in a metabolic condition of the patient.

34. The thermal therapy system of claim 30 wherein a core body temperature of the patient can be changed with an overshoot of less than 0.5 degrees Celsius and maintained within 0.2 degrees Celsius of a set temperature.

35. The thermal therapy system of claim 30
wherein the temperature control module operates in four states comprising:
a stable state when the monitored temperature is within 0.25 degrees Celsius of an ideal temperature;
a slow state when the monitored temperature is between 0.25 and 1.00 degrees Celsius of the ideal temperature;
a medium state when the monitored temperature is between 1.00 and 2.00 degrees Celsius of the ideal temperature; and
a fast state when the monitored temperature is more than 2.00 degrees Celsius away from the ideal temperature.

* * * * *